US011395486B2

(12) United States Patent
Tsushima et al.

(10) Patent No.: US 11,395,486 B2
(45) Date of Patent: Jul. 26, 2022

(54) ANTIBACTERIAL AND ANTIFUNGAL COMPOSITION

(71) Applicant: ADEKA CORPORATION, Tokyo (JP)

(72) Inventors: Yasuhiro Tsushima, Tokyo (JP); Hiroshi Suzuki, Tokyo (JP); Makiko Yazawa, Tokyo (JP); Shotan Yamashita, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 16/638,580

(22) PCT Filed: Aug. 8, 2018

(86) PCT No.: PCT/JP2018/029755
§ 371 (c)(1),
(2) Date: Feb. 12, 2020

(87) PCT Pub. No.: WO2019/044436
PCT Pub. Date: Mar. 7, 2019

(65) Prior Publication Data

US 2020/0214285 A1 Jul. 9, 2020

(30) Foreign Application Priority Data

Aug. 28, 2017 (JP) ............................. JP2017-163099

(51) Int. Cl.

| | |
|---|---|
| ***A01N 31/04*** | (2006.01) |
| ***A61K 8/34*** | (2006.01) |
| ***C11D 7/26*** | (2006.01) |
| ***A61P 31/04*** | (2006.01) |
| ***A61Q 19/00*** | (2006.01) |
| ***A61Q 17/00*** | (2006.01) |
| ***C11D 17/04*** | (2006.01) |
| ***C11D 3/48*** | (2006.01) |
| ***A61Q 19/10*** | (2006.01) |

(52) U.S. Cl.
CPC ................ *A01N 31/04* (2013.01); *A61K 8/34* (2013.01); *A61K 8/345* (2013.01); *A61P 31/04* (2018.01); *A61Q 17/005* (2013.01); *A61Q 19/00* (2013.01); *A61Q 19/10* (2013.01); *C11D 3/48* (2013.01); *C11D 7/26* (2013.01); *C11D 7/261* (2013.01); *C11D 7/263* (2013.01); *C11D 17/049* (2013.01)

(58) Field of Classification Search
CPC .. A01N 31/04; A61K 8/34; A61K 2800/5922; A61K 8/345; C11D 7/26; C11D 17/049; C11D 3/48; C11D 7/261; C11D 7/263; A61Q 19/10; A61Q 17/005; A61Q 19/00; A61P 31/04
See application file for complete search history.

(56) References Cited

U.S. PATENT DOCUMENTS 8,058,218 B2 * 11/2011 Beilfuss ................ A61K 8/345
510/130

FOREIGN PATENT DOCUMENTS

| | | |
|---|---|---|
| EP | 2 316410 | 5/2011 |
| JP | 10-53510 | 2/1998 |
| JP | 11-322591 | 11/1999 |
| JP | 2007-16018 | 1/2007 |
| JP | 2008-266332 | 11/2008 |
| JP | 2012-527411 | 11/2012 |
| JP | 2014-5209 | 1/2014 |
| JP | 2017-25005 | 2/2017 |
| KR | 10-2017-0055877 | 5/2017 |
| WO | 2016/164205 | 10/2016 |

OTHER PUBLICATIONS

International Search Report dated Nov. 6, 2018 in International (PCT) Application No. PCT/JP2018/029755.
Night cream, database GNPD [online], Mintel, Jul. 2016, [retrieved on Oct. 19, 2018], entire text, URL: http://www.gnpd.com/sinatra/recordpage/4149111/from_search/PJTBEytvcQ/?page=1 (database accession No. 4149111).
"Moisturising Liquid Hand Soap", Mintel, Database GNPD [Online], Apr. 2016, XP055800959, Database accession No. 3957747.
"Active & Pure Deodorant Spray", Mintel, Database GNPD [Online], Mar. 2017, XP055800970, Database accession No. 4686545.
Varvaresou et al., "Self-preserving cosmetics", International Journal of Cosmetic Science, 2009, vol. 31, No. 3., pp. 163-175.
Woodruff, J., "Cosmetic Preservation", 2016, XP055432565, Retrieved from the Internet: URL: http://creative-developments.co.uk/wp-content/uploads/2013/10/Cosmetic-Preservation-2016.pdf, 8 pages.

(Continued)

*Primary Examiner* — Mina Haghighatian
*Assistant Examiner* — Andriae M Holt
(74) *Attorney, Agent, or Firm* — Wenderoth, Lind & Ponack, L.L.P.

(57) ABSTRACT

Provided is an antibacterial and antifungal composition, including: (A) at least one kind of 1,2-alkanediol having a linear alkyl group containing 6 to 8 carbon atoms; (B) at least one kind of monoalkyl glyceryl ether having a linear alkyl group containing 6 to 8 carbon atoms, a branched alkyl group containing 6 to 8 carbon atoms, or a cycloalkyl group containing 6 to 8 carbon atoms; and (C) at least one kind of aromatic alcohol represented by the following general formula (1):

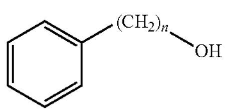

(1)

wherein n represents a natural number of from 1 to 4.

4 Claims, No Drawings

(56) References Cited

OTHER PUBLICATIONS

Extended European Search Report dated May 18, 2021 in corresponding European Patent Application No. 18851722.1.

* cited by examiner

ANTIBACTERIAL AND ANTIFUNGAL COMPOSITION

TECHNICAL FIELD

The present invention relates to an antibacterial and antifungal composition having high antibacterial properties and antifungal properties while having high safety to a human body.

BACKGROUND ART

In general, an antibacterial agent and an antifungal agent are used in a cosmetic preparation, a cleaning agent, and the like, for example, for antiseptic purposes. As such antibacterial and antifungal agents, parabens have been used. However, in recent years, the number of people who undergo an allergic reaction to parabens is increasing, and hence there has been a demand for an antibacterial and antifungal agent in which parabens are not blended, and which has high safety to a human body.

In view of the foregoing, it has been known that a diol compound, such as alkanediols and alkyl glyceryl ethers, and a mixture thereof are used as an antibacterial agent. Patent Document 1 discloses an antibacterial agent consisting of a diol compound having a residue obtained by removing one hydroxy group from a trihydric or higher alcohol. Patent Document 2 discloses an external composition containing 1,2-pentanediol and 2-phenoxyethanol. Patent Document 3 discloses an antiseptic bactericide obtained by combining a 1,2-alkanediol with one or more kinds of photosensitizer 201, benzoic acid and a salt thereof, phenoxyethanol, and 4-isopropyl-3-methylphenol. Patent Document 4 discloses an antibacterial composition containing an alkanediol compound and a glyceryl ether compound, and a cationic β-glucan. Those compositions do not use parabens, and hence are considered to have satisfactory performance as an antibacterial agent while having high safety to a human body.

CITATION LIST

Patent Document

Patent Document 1: JP 2007-016018 A

Patent Document 2: JP H10-053510 A

Patent Document 3: JP H11-322591 A

Patent Document 4: JP 2014-005209 A

SUMMARY OF INVENTION

Technical Problem

However, although the conventional antibacterial agents have high safety to a human body, they may not have sufficient antibacterial properties and antifungal properties for use as antibacterial and antifungal agents and they are required to be used in a large amount when used in a cosmetic preparation, a cleaning agent, and the like. Therefore, there has been a demand for improvement of antibacterial performance and antifungal performance from the market. An object of the present invention is to provide an antibacterial and antifungal composition having high antibacterial properties and antifungal properties while having high safety to a human body.

Solution to Problem

In view of the foregoing, the inventors of the present invention have made extensive investigations, and as a result, have found an antibacterial and antifungal composition having high antibacterial properties and antifungal properties without using parabens, to thereby achieve the present invention.

That is, the present invention is directed to an antibacterial and antifungal composition, comprising: (A) at least one kind of 1,2-alkanediol having a linear alkyl group containing 6 to 8 carbon atoms; (B) at least one kind of monoalkyl glyceryl ether having a linear alkyl group containing 6 to 8 carbon atoms, a branched alkyl group containing 6 to 8 carbon atoms, or a cycloalkyl group containing 6 to 8 carbon atoms; and (C) at least one kind of aromatic alcohol represented by the following general formula (1):

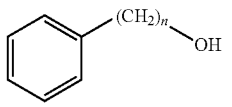

(1)

In the formula, n represents a natural number of from 1 to 4.

Advantageous Effects of Invention

According to the present invention, the antibacterial and antifungal composition having high antibacterial properties and antifungal properties while having high safety to a human body can be provided. In addition, the antibacterial and antifungal composition of the present invention is less irritant to, in particular, the skin, and is excellent in moisture retention performance. Therefore, the antibacterial and antifungal composition of the present invention can be suitably formulated for a cosmetic preparation and a cleaning agent.

DESCRIPTION OF EMBODIMENTS

Component (A) used in the present invention is a 1,2-alkanediol having a linear alkyl group containing 6 to 8 carbon atoms. Examples of such 1,2-alkanediol include 1,2-hexanediol, 1,2-heptanediol, and 1,2-octanediol. Those 1,2-alkanediols may be used alone or in combination thereof. Of those, 1,2-octanediol is preferred from the viewpoint of high antibacterial and antifungal properties obtained through exhibition of the enhancing effect of Component (C) on antibacterial and antifungal properties.

Component (B) used in the present invention is a monoalkyl glyceryl ether having a linear alkyl group containing 6 to 8 carbon atoms, a branched alkyl group containing 6 to 8 carbon atoms, or a cycloalkyl group containing 6 to 8 carbon atoms. Examples of such linear alkyl group, branched alkyl group, and cycloalkyl group include a hexyl group, a secondary hexyl group, a heptyl group, a secondary heptyl group, an octyl group, a 2-ethylhexyl group, a secondary octyl group, a cyclohexyl group, a methylcyclohexyl group, a dimethylcyclohexyl group, a cycloheptyl group, and a methylcycloheptyl group. When the number of carbon atoms is less than 6, the antibacterial properties are decreased, and hence the resultant composition cannot withstand actual use. On the other hand, when the number of carbons is more than 8, the resultant composition is strongly irritant to the skin in addition to a decrease in antibacterial properties. Moreover, solubility of the composition in water is degraded, and hence it is difficult to blend the composition in a product of an aqueous solution. Monoalkyl glyceryl ethers having the above-mentioned linear alkyl groups, branched alkyl groups, or cycloalkyl groups may be used alone or in combination thereof. Of those, 2-ethylhexyl glyceryl ether is preferred from the viewpoint of high antibacterial and antifungal properties obtained through exhibition of the enhancing effect of Component (C) on antibacterial and antifungal properties.

Component (C) used in the present invention is an aromatic alcohol represented by the following general formula (1):

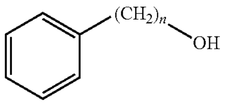

(1)

In the formula, n represents a natural number of from 1 to 4. Examples of such aromatic alcohol include benzyl alcohol (n=1), phenethyl alcohol (n=2), 3-phenylpropyl alcohol (n=3), and 4-phenylbutyl alcohol (n=4). Those aromatic alcohols may be used alone or in combination thereof. Of those, at least one kind selected from the group consisting of benzyl alcohol and phenethyl alcohol is preferred from the viewpoints of the enhancing effect on antibacterial properties and antifungal properties of Component (A) and Component (B), availability, and the like. Through use of Component (C) formed of such specific aromatic alcohol, there can be obtained a composition that exhibits high antibacterial properties and antifungal properties, in particular, antibacterial properties and antifungal properties against many kinds of bacteria and fungi, as compared to the case of using a compound such as phenoxyethanol.

The antibacterial and antifungal composition of the present invention contains Component (A), Component (B), and Component (C). When the antibacterial and antifungal composition contains such three kinds of components, the antibacterial and antifungal composition can show a specific synergistic effect and exhibit high antibacterial properties and antifungal properties.

It has been known that Component (A) and Component (B) each have an antibacterial effect. When Component (A) and Component (B) are used together with Component (C), the antibacterial properties and antifungal properties are significantly improved, as compared to a composition containing Component (A) alone, a composition containing Component (B) alone, and a composition containing Component (A) and Component (B). When both Component (A) and Component (B) are not blended, significant improvement of the antibacterial properties and the antifungal properties cannot be expected.

There is no particular limitation on the amount of each of the components (A) to (C) in the antibacterial and antifungal composition of the present invention. The content of Component (C) is preferably from 10 parts by mass to 1,000 parts by mass, more preferably from 20 parts by mass to 800 parts by mass, still more preferably from 25 parts by mass to 500 parts by mass, yet still more preferably from 33 parts by mass to 200 parts by mass, most preferably from 33 parts by mass to 100 parts by mass, when the total mass of Component (A) and Component (B) is 100 parts by mass. When the content of Component (C) falls within the above-mentioned range, the antibacterial and antifungal effect of Component (A) and Component (B) can be particularly enhanced by Component (C). Thus, the antibacterial properties and antifungal properties of the antibacterial and antifungal composition become particularly satisfactory through the above-mentioned synergistic effect. In addition, from the viewpoint of satisfying both the antibacterial properties and the antifungal properties, and the safety to a human body, the mass ratio between Component (A) and Component (B) in the antibacterial and antifungal composition is preferably from 20:80 to 80:20 (total mass ratio is 100), more preferably from 33:67 to 67:33 (total mass ratio is 100). When the mass ratio between Component (A) and Component (B) falls within the above-mentioned range, the antibacterial properties and the antifungal properties of the antibacterial and antifungal composition become particularly satisfactory. When each component is formed of two or more kinds of compounds, the total mass thereof is defined as the content of the component. In addition, regarding the content of each of Component (A), Component (B), and Component (C) in the antibacterial and antifungal composition, when the total mass of Component (A), Component (B), and Component (C) is 100 parts by mass, the contents of Component (A), Component (B), and Component (C) preferably fall within ranges of from 5 parts by mass to 60 parts by mass, from 5 parts by mass to 60 parts by mass, and from 10 parts by mass to 90 parts by mass, respectively, and the contents of Component (A), Component (B), and Component (C) more preferably fall within ranges of from 20 parts by mass to 50 parts by mass, from 20 parts by mass to 50 parts by mass, and from 15 parts by mass to 40 parts by mass, respectively. When the content of each of Component (A), Component (B), and Component (C) falls within the above-mentioned range, the antibacterial and antifungal effect of Component (A) and Component (B) can be effectively utilized, and the enhancing effect of Component (C) on the antibacterial and antifungal effect of Component (A) and Component (B) can also be effectively utilized.

There is no particular limitation on the pH of the antibacterial and antifungal composition of the present invention. The pH is preferably from 2 to 12, more preferably from 3 to 11 from the viewpoints of storage stability and safety.

The antibacterial and antifungal composition of the present invention can be used for the same purposes and applications as those of known antibacterial agents, antifungal agents, bactericides, and disinfectants. For example, the antibacterial and antifungal composition of the present invention can be used in a cosmetic preparation, a medical cleaning agent, a household cleaning agent, a cleaning agent for food industry, an antibacterial agent for subjecting a synthetic resin and daily commodities to antibacterial finishing, an aqueous or non-aqueous coating material, a medical softener, and the like. Due to high safety to a human body, the antibacterial and antifungal composition of the present invention can be suitably used in, of those, a cleaning agent, a cosmetic preparation, and the like which are brought into direct contact with a human body. In addition, there is no particular limitation on the usage of a cosmetic preparation, a cleaning agent, an antibacterial agent, a coating material, a medical softener, and the like containing the antibacterial and antifungal composition of the present invention. For example, there can be used a method involving spraying the antibacterial and antifungal composition on an object to be subjected to antibacterial treatment, a method involving applying the antibacterial and antifungal composition to the object, a method involving applying the antibacterial and antifungal composition to the object under a state in which the antibacterial and antifungal composition is impregnated into foundation cloth or the like, a method involving impregnating the antibacterial and antifungal composition into the object, a method involving immersing the object in the antibacterial and antifungal composition, a method involving blending the antibacterial and antifungal composition at a time of molding and processing or preparing the object, and the like. In addition, the antibacterial and antifungal composition of the present invention may contain other components in accordance with applications as long as the effect of the present invention is not impaired.

A cosmetic preparation of the present invention is a cosmetic preparation containing the antibacterial and antifungal composition of the present invention. Examples of such cosmetic preparation include a face-washing cream, a face-washing foam, a cleansing cream, a cleansing milk, a cleansing lotion, a massage cream, a cold cream, a moisture cream, a shaving cream, a sunscreen cream, a hair tonic, a hair cream, a hair liquid, a set lotion, a hair bleach, a color rinse, a permanent wave solution, a hand cream, a lipstick, various packs, a foundation, a cosmetic lotion, a cosmetic liquid, a milky lotion, eau de cologne, a nail cosmetic, and a chemical agent for sanitary products, such as wet wipes or antibacterial wipes. There is no particular limitation on the blending amount of the antibacterial and antifungal composition of the present invention as long as the blending amount is an amount that enables the intended antibacterial properties and antifungal properties to be exhibited, and the blending amount may be appropriately regulated in accordance with applications. From the viewpoint of satisfying both the antibacterial properties and antifungal properties and the safety, the blending amount of the antibacterial and antifungal composition of the present invention is preferably from 0.001 mass % to 10 mass %, more preferably from 0.01 mass % to 3.0 mass %, most preferably from 0.1 mass % to 2.0 mass % with respect to the entire cosmetic preparation.

The cosmetic preparation of the present invention may contain other components in accordance with intended uses as long as the effect of the antibacterial and antifungal composition of the present invention is not impaired. The cosmetic preparation may appropriately have blended therein, for example, one kind or two or more kinds of a powder component, a liquid oil and fat, a solid oil and fat, wax, a hydrocarbon, a higher fatty acid, a higher alcohol, an ester, silicone, an anionic surfactant, a cationic surfactant, an amphoteric surfactant, a non-ionic surfactant, a moisturizer, a water-soluble polymer, a chelating agent, a lower alcohol, a polyhydric alcohol (except Component (A) and Component (B) in the present invention), a sugar, an amino acid, an organic amine, a polymer emulsion, a pH adjusting agent, a skin nutrient, a vitamin, and an antioxidant, as required. The abbreviation "POE" represents "polyoxyethylene" and the abbreviation "POP" represents "polyoxypropylene" in the following description.

Examples of the powder component include: inorganic powders (for example, talc, kaolin, mica, sericite, white mica, bronze mica, synthetic mica, lepidolite, black mica, vermiculite, magnesium carbonate, calcium carbonate, aluminum silicate, barium silicate, calcium silicate, magnesium silicate, strontium silicate, a metal salt of tungstic acid, magnesium, silica, zeolite, barium sulfate, calcined calcium sulfate (calcined gypsum), calcium phosphate, fluorine apatite, hydroxyapatite, ceramic powder, metal soap (for example, zinc myristate, calcium palmitate, or aluminum stearate), and boron nitride); organic powders (for example, polyamide resin powder (nylon powder), polyethylene powder, polymethyl methacrylate powder, polystyrene powder, copolymer resin powder of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and yellow ocher); inorganic black pigments (for example, black iron oxide and lower titanium oxide); inorganic purple pigments (for example, manganese violet and cobalt violet); inorganic green pigments (for example, chromium oxide, chromium hydroxide, and cobalt titanate); inorganic blue pigments (for example, ultramarine blue and Prussian blue); pearl pigments (for example, titanium oxide-coated mica, titanium oxide-coated bismuth oxychloride, titanium oxide-coated talc, colored titanium oxide-coated mica, bismuth oxychloride, and argentine); metal powder pigments (for example, aluminum powder and copper powder); organic pigments, such as zirconium, barium, and aluminum lakes (for example, organic pigments, such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, and Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural coloring matter (for example, chlorophyl and β-carotene).

Examples of the liquid oil and fat include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japan tung oil, jojoba oil, germ oil, and triglycerin.

Examples of the solid oil and fat include cacao butter, coconut oil, hydrogenated coconut oil, palm oil, palm kernel oil, Japan wax kernel oil, hydrogenated oil, Japan wax, and hydrogenated castor oil.

Examples of the wax include beeswax, candelilla wax, cotton wax, carnauba wax, bayberry wax, privet wax, spermaceti, montan wax, bran wax, lanolin, kapok wax, lanolin acetate, liquid lanolin, sugar cane wax, a lanolin fatty acid isopropyl ester, hexyl laurate, reduced lanolin, jojoba wax, hard lanolin, shellac wax, a POE lanolin alcohol ether, a POE lanolin alcohol acetate, a POE cholesterol ether, a lanolin fatty acid polyethylene glycol, and a POE hydrogenated lanolin alcohol ether.

Examples of the hydrocarbon oil include liquid paraffin, ozocerite, squalane, pristane, paraffin, ceresin, squalene, Vaseline, and microcrystalline wax.

Examples of the higher fatty acid include lauric acid, myristic acid, palmitic acid, stearic acid, behenic acid, oleic acid, undecylenic acid, a tall oil fatty acid, isostearic acid, linoleic acid, linolenic acid, eicosapentaenoic acid (EPA), and docosahexaenoic acid (DHA).

Examples of the higher alcohol include: linear alcohols (for example, lauryl alcohol, cetyl alcohol, stearyl alcohol, behenyl alcohol, myristyl alcohol, oleyl alcohol, and cetostearyl alcohol); and branched alcohols (for example, 2-decyltetradecinol, lanolin alcohol, cholesterol, phytosterol, hexyl dodecanol, isostearyl alcohol, and octyl dodecanol).

Examples of the ester oil include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, glyceryl di-2-ethylhexanoate, a dipentaerythritol fatty acid ester, glyceryl monoisostearate, neopentyl glycol dicaprate, diisostearyl malate, glyceryl di-2-heptylundecanoate, trimethylolpropane tri-2-ethylhexanoate, trimethyolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, 2-ethylhexyl palmitate, glyceryl trimyristate, glyceryl tri-2-heptylundecanoate, a castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, and 2-ethylhexyl succinate.

Examples of the silicone oil include: chain polysiloxanes (for example, dimethylpolysiloxane, methylphenylpolysiloxane, and diphenylpolysiloxane); ring polysiloxanes (for example, octamethylcyclotetrasiloxane, decamethylcyclopentasiloxane, and dodecamethylcyclohexasiloxane); silicone resins forming a three-dimensional network structure; silicone rubbers; and various modified polysiloxanes (an amino-modified polysiloxane, a polyether-modified polysiloxane, an alkyl-modified polysiloxane, a fluorine-modified polysiloxane, and the like).

Examples of the anionic surfactant include: fatty acid soaps (such as sodium laurate and sodium palmitate); higher alkyl sulfuric acid ester salts (such as sodium lauryl sulfate and potassium lauryl sulfate); alkyl ether sulfuric acid ester salts (such as POE-lauryl sulfate triethanolamine and POE-sodium lauryl sulfate); N-acylsarcosinates (such as sodium lauroylsarcosine); higher fatty acid amide sulfonic acid salts (such as N-myristoyl-N-methyl taurine sodium, coconut oil fatty acid methyl taurine sodium, and lauryl methyl taurine sodium); phosphoric acid ester salts (POE-sodium oleyl ether phosphate, POE-stearyl ether phosphoric acid, and the like); sulfosuccinic acid salts (such as sodium di-2-ethylhexyl sulfosuccinate, sodium monolauroyl monoethanolamide polyoxyethylene sulfosuccinate, and sodium lauryl polypropylene glycol sulfosuccinate); alkyl benzenesulfonic acid salts (such as sodium linear dodecylbenzenesulfonate, triethanolamine linear dodecylbenzenesulfonate, and linear dodecylbenzenesulfonic acid); higher fatty acid ester sulfuric acid ester salts (such as sodium hydrogenated coconut oil fatty acid glycerin sulfate); N-acyl glutamic acid salts (such as monosodium N-lauroyl glutamate, disodium N-stearoyl glutamate, and monosodium N-myristoyl-L-glutamate); sulfonated oils (such as Turkey red oil); POE-alkyl ether carboxylic acids; POE-alkyl allyl ether carboxylic acid salts; α-olefin sulfonic acid salts; higher fatty acid ester sulfonic acid salts; secondary alcohol sulfuric acid ester salts; higher fatty acid alkylolamide sulfuric acid ester salts; sodium lauroyl monoethanolamide succinate; N-palmitoyl aspartate ditriethanolamine; and casein sodium.

Examples of the cationic surfactant include: alkyltrimethylammonium salts (such as stearyltrimethylammonium chloride and lauryltrimethylammonium chloride); alkylpyridinium salts (such as cetylpyridinium chloride); distearyldimethylammonium dialkyldimethylammonium chloride salts; poly(N,N'-dimethyl-3,5-methylenepiperidinium) chloride; alkyl quaternary ammonium salts; alkyldimethylbenzylammonium salts; alkylisoquinolinium salts; dialkylmorpholinium salts; POE-alkylamines; alkylamine salts; polyamine fatty acid derivatives; amyl alcohol fatty acid derivatives; benzalkonium chloride; and benzethonium chloride.

Examples of the amphoteric surfactant include: imidazoline-based amphoteric surfactants (such as sodium 2-undecyl-N,N,N-(hydroxyethylcarboxymethyl)-2-imidazoline, and 2-cocoyl-2-imidazolium hydroxide-1-carboxyethyloxy disodium salt); and betaine-based surfactants (such as a 2-alkyl-N-carboxymethyl-N-hydroxyethylimidazolium betaine (sodium cocoamphoacetate), betaine lauryldimethylaminoacetate, an alkylbetaine, amidobetaine, and sulfobetaine).

Examples of the non-ionic surfactant include: sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerin polyglycerin fatty acids (such as a monocottonseed oil fatty acid glycerin, glycerin monoerucate, glycerin sesquioleate, glycerin monostearate, glycerin α,α'-oleate pyroglutamate, and glycerin monostearate malate); propylene glycol fatty acid esters (such as propylene glycol monostearate); hydrogenated castor oil derivatives; glycerin alkyl ethers; POE-sorbitan fatty acid esters (such as POE-sorbitan monooleate, POE-sorbitan monostearate, and POE-sorbitan tetraoleate); POE-sorbit fatty acid esters (such as POE-sorbit monolaurate, POE-sorbit monooleate, POE-sorbit pentaoleate, and POE-sorbit monostearate); POE-glycerin fatty acid esters (such as POE-monooleates, e.g., POE-glycerin monostearate, POE-glycerin monoisostearate, and POE-glycerin triisostearate); POE-fatty acid esters (such as POE-distearate, POE-monodioleate, and ethylene glycol distearate); POE-alkyl ethers (such as POE-lauryl ether, POE-oleyl ether, POE-stearyl ether, POE-behenyl ether, POE-2-octyldodecyl ether, and POE-cholestanol ether); Pluronic-type surfactants (such as Pluronic); POE/POP-alkyl ethers (such as POE/POP-cetyl ether, POE/POP-2-decyl tetradecyl ether, POE/POP-monobutyl ether, POE/POP-hydrogenated lanolin, and POE/POP-glycerin ether); tetra POE/tetra POP-ethylenediamine condensates (such as Tetronic); POE-castor oil/hydrogenated castor oil derivatives (such as POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, and POE-hydrogenated castor oil maleic acid ester); POE-beeswax/lanolin derivatives (such as POE-sorbit beeswax); alkanolamides (such as coconut oil fatty acid diethanolamides, lauric acid monoethanol amide, and a fatty acid isopropanolamide); POE-propylene glycol fatty acid esters; POE-alkylamines; POE-fatty acid amides; sucrose fatty acid esters; alkylethoxydimethylamine oxides; and trioleyl phosphate.

Examples of the moisturizer include polyethylene glycol, xylitol, sorbitol, maltitol, chondroitin sulfate, hyaluronic acid, mucoitin sulfate, charonic acid, atelocollagen, cholesteryl-12-hydroxystearate, sodium lactate, a bile acid salt, a dl-pyrrolidonecarboxylic acid salt, short-chain soluble collagen, a diglycerin (EO)PO adduct, a *Rosa roxburghii* extract, a yarrow extract, and a sweet clover extract.

As a natural water-soluble polymer, there are given, for example: plant-based polymers (such as gum arabic, tragacanth gum, galactan, guar gum, carob gum, gum karaya, carrageenan, pectin, agar, a quince seed (quince), algae colloid (brown alga extract), starch (rice, corn, potato, and wheat), and glycyrrhizic acid); microorganism-based polymers (such as xanthane gum, dextran, succinoglucan, pullulan, and gellan gum); and animal-based polymers (such as collagen, casein, albumin, and gelatin).

Examples of the water-soluble polymer include: starch-based polymers (such as carboxymethyl starch and methylhydroxypropyl starch); cellulose-based polymers (such as methylcellulose, ethylcellulose, methylhydroxypropylcellulose, hydroxyethylcellulose, sodium cellulose sulfate, hydroxypropylcellulose, carboxymethylcellulose, sodium carboxymethylcellulose, crystalline cellulose, and cellulose powder); alginic acid-based polymers (such as sodium alginate and propylene glycol alginate ester); vinyl-based polymers (such as polyvinyl alcohol, polyvinyl methyl ether, polyvinylpyrrolidone, and a carboxyvinyl polymer); polyoxyethylene-based polymers (such as polyoxyethylene-polyoxypropylene copolymers of polyethylene glycol 20,000, 40,000, or 60,000); acrylic polymers (such as sodium polyacrylate, polyethyl acrylate, and polyacrylamide); polyethylene imine; and cationic polymers.

Examples of the chelating agent include 1-hydroxyethane-1,1-diphosphonic acid, 1-hydroxyethane-1,1-diphosphonic acid tetrasodium salts, disodium edetate, trisodium edetate, tetrasodium edetate, sodium polyphosphate, sodium metaphosphate, phosphoric acid, ascorbic acid, succinic acid, and edetic acid.

Examples of the lower alcohol include ethanol, propanol, isopropanol, isobutyl alcohol, and t-butyl alcohol.

Examples of the polyhydric alcohol include: dihydric alcohols (such as 1,2-ethanediol, 1,2-propanediol, 1,3-propanediol, 1,2-butanediol, 1,3-butanediol, 1,4-butanediol, 2,3-butanediol, 1,2-pentanediol, 1,5-pentanediol, and 2,4-pentanediol); trihydric alcohols (such as glycerin and trimethylolpropane); tetrahydric alcohols (such as 1,2,5,6-hexanetetraol and pentaerythritol); pentahydric alcohols (such as xylitol); hexahydric alcohols (such as sorbitol and mannitol); polyhydric alcohol polymers (such as diethylene glycol, triethylene glycol, dipropylene glycol, polypropylene glycol, tetraethylene glycol, diglycerin, polyethylene glycol, triglycerin, tetraglycerin, and polyglycerin); alcohol alkyl ethers (such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); sugar alcohols (such as sorbitol, maltitol, maltotriose, mannitol, sucrose, erythritol, glucose, fructose, amylolysis sugars, maltose, xylitose, and alcohols prepared by reduction of amylolysis sugars); Glysolid; tetrahydrofurfuryl alcohol; POE-tetrahydrofurfuryl alcohol; POP-butyl ether; POP/POE-butyl ether; tripolyoxypropylene glycerin ether; POP-glycerin ether; POP-glycerin ether phosphate; POP/POE-pentaneerythritol ether; and polyglycerin.

As a monosaccharide, there are given, for example: trioses (such as D-glyceryl aldehyde and dihydroxyacetone); tetroses (such as D-erythrose, D-erythrulose, D-threose, and erythritol); pentoses (such as L-arabinose, D-xylose, L-lixose, D-arabinose, D-ribose, D-ribulose, D-xylulose, and L-xylulose); hexoses (such as D-glucose, D-talose, D-psicose, D-galactose, D-fructose, L-galactose, L-mannose, and D-tagatose); heptoses (such as aldoheptose and heptulose); octoses (such as octulose); deoxy sugars (such as 2-deoxy-D-ribose, 6-deoxy-L-galactose, and 6-deoxy-L-mannose); amino sugars (such as D-glucosamine, D-galactosamine, sialic acid, aminouronic acid, and muramic acid); and uronic acids (such as D-glucuronic acid, D-mannuronic acid, L-guluronic acid, D-galacturonic acid, and L-iduronic acid).

As an oligosaccharide, there are given, for example, sucrose, umbelliferose, lactose, planteose, isolychnoses, α,α-trehalose, raffinose, lychnoses, umbilicin, and stachyose-verbascoses.

As a polysaccharide, there are given, for example, cellulose, quince seed, chondroitin sulfate, starch, galactan, dermatan sulfate, glycogen, gum arabic, heparan sulfate, hyaluronic acid, tragacanth gum, keratan sulfate, chondroitin, xanthane gum, mucoitin sulfate, guar gum, dextran, keratosulfate, locust bean gum, succinoglucan, and charonic acid.

Examples of the amino acid include: neutral amino acids (such as threonine and cysteine); and basic amino acids (such as hydroxylysine). In addition, as an amino acid derivative, there are given, for example, acylsarcosine sodium (lauroylsarcosine sodium), acylglutamic acid salts, acyl β-alanine sodium, glutathione, and pyrrolidone carboxylic acid.

Examples of the organic amine include monoethanol amine, diethanol amine, triethanol amine, morpholine, triisopropanolamine, 2-amino-2-methyl-1,3-propanediol, and 2-amino-2-methyl-1-propanol.

Examples of the polymer emulsion include an acrylic resin emulsion, a polyethyl acrylate emulsion, an acrylic resin liquid, a polyacrylic alkyl ester emulsion, a polyvinyl acetate resin emulsion, and a natural rubber latex.

Examples of the pH adjusting agent include lactic acid-sodium lactate, succinic acid-sodium succinate, citric acid-sodium citrate, and sodium hydrogen carbonate. It is only required that the pH of the cosmetic preparation of the present invention be appropriately regulated in accordance with applications. The pH of the cosmetic preparation of the present invention is preferably from 3.0 to 7.5 from the viewpoint of applicability to the skin or the like.

Examples of the vitamin include vitamins A, B1, B2, B6, C, and E, and derivatives thereof, pantothenic acid and a derivative thereof, and biotin.

Examples of the antioxidant include tocopherols, dibutylhydroxytoluene, butylhydroxyanisole, and gallic acid esters.

Examples of other blendable components include: antiphlogistic agents (such as glycyrrhizic acid derivatives, glycyrrhetinic acid derivatives, salicylic acid derivatives, hinokitiol, zinc oxide, and allantoin); whitening agents (such as a saxifrage extract and arbutin); various extracts (extracts of *Phellodendron bark, Coptis japonica*, lithospermum root, *Paeonia lactiflora, Swertia japonica*, birch, sage, loquat, carrot, aloe, mallow, iris, grapevine, coix seed, dishcloth gourd, lily, saffron, *Cnidium rhizome*, ginger, hypericum, *Ononis spinosa*, garlic, capsicum, *Citrus unshiu* peel, *Angelica acutiloba*, seaweed, or the like); activators (such as royal jelly, a photosensitizer, and cholesterol derivatives); circulation promoters (such as benzyl nicotinate ester, β-butoxyethyl nicotinate ester, capsaicin, zingerone, Cantharides tincture, ichthammol, tannic acid, α-borneol, tocopherol nicotinate, inositol hexanicotinate, cyclandelate, cinnarizine, tolazoline, acetylcholine, verapamil, cepharanthine, and γ-orizanol); antiseborrheic agents (such as sulfur and thianthol); and anti-inflammatory agents (such as tranexamic acid, thiotaurine, and hypotaurine).

The cleaning agent of the present invention is a cleaning agent containing the antibacterial and antifungal composition of the present invention and a surfactant. As such cleaning agent, there are given, for example: household cleaning agents, such as a kitchen cleaning agent, a toilet cleaning agent, and a bathroom cleaning agent; and body cleaning agents, such as a shampoo, a rinse, hand soap, and body soap. There is no particular limitation on the blending amount of the antibacterial and antifungal composition of the present invention as long as the blending amount is an amount that enables the intended antibacterial properties and antifungal properties to be exhibited, and the blending amount may be appropriately regulated in accordance with applications. From the viewpoint of satisfying both the antibacterial properties and antifungal properties and the safety, the blending amount of the antibacterial and antifungal composition of the present invention is, for example, from 0.001 mass % to 10 mass %, preferably from 0.01 mass % to 3.0 mass %, particularly preferably from 0.1 mass % to 2.0 mass %.

As the surfactant that may be used in the cleaning agent of the present invention, there are given, for example, an anionic surfactant, a cationic surfactant, and a non-ionic surfactant. Of those, in particular, the anionic surfactant or the non-ionic surfactant is preferably used as the cleaning agent of the present invention.

Examples of the anionic surfactant include a higher fatty acid salt, a higher alcohol sulfuric acid ester salt, a sulfurized olefin salt, a higher alkyl sulfonic acid salt, an α-olefin sulfonic acid salt, a sulfated fatty acid salt, a sulfonated fatty acid salt, a phosphoric acid ester salt, a sulfuric acid ester salt of a fatty acid ester, a glyceride sulfuric acid ester salt, a sulfonic acid salt of a fatty acid ester, an α-sulfofatty acid methyl ester salt, a polyoxyalkylene alkyl ether sulfuric acid ester salt, a polyoxyalkylene alkylphenyl ether sulfuric acid ester salt, a polyoxyalkylene alkyl ether carboxylic acid salt, an acylated peptide, a sulfuric acid ester salt of a fatty acid alkanolamide or an alkylene oxide adduct thereof, a sulfosuccinic acid ester salt, an alkylbenzene sulfonic acid salt, an alkylnaphthalene sulfonic acid salt, an alkylbenzimidazole sulfonic acid salt, a polyoxyalkylene sulfosuccinic acid salt, a salt of an N-acyl-N-methyl taurine, an N-acylglutamic acid or a salt thereof, an acyloxyethane sulfonic acid salt, an alkoxyethane sulfonic acid salt, an N-acyl-β-alanine or a salt thereof, an N-acyl-N-carboxyethyl taurine or a salt thereof, an N-acyl-N-carboxymethyl glycine or a salt thereof, an acyllactic acid salt, an N-acylsarcosine salt, and an alkyl or alkenyl aminocarboxymethyl sulfuric acid salt. As a counter ion of such salt of the anionic surfactant, there are given, for example: alkali metal ions, such as lithium, sodium, and potassium; alkaline earth metal ions, such as calcium and magnesium; ammonium; and organic ammoniums, such as monoethanolammonium, diethanolammonium, triethanolammonium, monoisopropanolammonium, diisopropanolammonium, and triisopropanolammonium.

As the higher fatty acid salt, a salt of a fatty acid containing 12 to 18 carbon atoms is preferred, and a coconut oil fatty acid salt, a dodecanoic acid salt, a tetradecanoic acid salt, a hexadecanoic acid salt, and an oleic acid salt are more preferred. Similarly, as the higher alkyl sulfuric acid ester salt, a higher alkyl sulfuric acid ester salt having an alkyl containing 10 to 18 carbon atoms is preferred, and a higher alkyl sulfuric acid ester salt having an alkyl containing 12 to 16 carbon atoms is more preferred. As a polyoxyethylene alkyl ether sulfuric acid ester salt, a polyoxyethylene alkyl ether sulfuric acid ester salt having an alkyl containing 10 to 18 carbon atoms is preferred, and a polyoxyethylene alkyl ether sulfuric acid ester salt having an alkyl containing 12 to 16 carbon atoms is more preferred. In addition, the average polymerization degree of a polyoxyethylene group is preferably from 1 to 12, more preferably from 2 to 10, still more preferably from 3 to 8.

Of those anionic surfactants, a higher fatty acid salt, a higher alkyl sulfuric acid ester salt, an α-sulfofatty acid methyl ester salt, a higher alcohol sulfuric acid ester salt, a polyoxyethylene alkyl ether sulfuric acid ester salt, a polyoxyethylene sulfosuccinic acid alkyl ester salt, and a monoalkyl phosphoric acid ester salt are preferred, and a higher fatty acid salt, a higher alkyl sulfuric acid ester salt, and a polyoxyethylene alkyl ether sulfuric acid ester salt are more preferred because of having low irritation to the skin and the like. In addition, for the same reason, a sodium ion, a potassium ion, ammonium, and triisopropanolammonium are preferred as the counter ion of the salt of the anionic surfactant.

In addition, examples of the non-ionic surfactant include a polyoxyalkylene alkyl ether, a polyoxyalkylene alkenyl ether, a polyoxyethylene polyoxypropylene alkyl ether (ethylene oxide and propylene oxide may be added in a random or block form), a propylene oxide adduct of polyethylene glycol, an ethylene oxide adduct of polypropylene glycol, a glycerin fatty acid ester or an ethylene oxide adduct thereof, a sorbitan fatty acid ester, a polyoxyethylene sorbitan fatty acid ester, an alkylpolyglucoside, a sucrose fatty acid ester, an alkyl(poly)glycerin ether, a polyglycerin fatty acid ester, a polyethylene glycol fatty acid ester, and a fatty acid methyl ester ethoxylate.

In the cleaning agent of the present invention, other components may be appropriately blended in addition to the above-mentioned surfactant components as long as the object of the present invention is not impaired. Examples of the other components include silicone oil, a thickener, an oil agent, powders (a pigment, a dye, and a resin), other antibacterial agents, a fragrance, a moisturizer, a physiologically active ingredient, salts, a solvent, an antioxidant, a chelating agent, a pearling agent, a neutralizing agent, a pH adjusting agent, and an enzyme. It is only required that the pH of the cleaning agent of the present invention be appropriately regulated in accordance with applications. The pH of the cleaning agent of the present invention is preferably from 6.0 to 12 from the viewpoint of cleaning properties or the like.

Examples of the thickener include a dimethyldiallylammonium chloride-acrylamide copolymer, an acrylamide-acrylic acid-dimethyldiallylammonium chloride copolymer, cellulose or a derivative thereof, keratin and collagen or derivatives thereof, calcium alginate, pullulan, agar, gelatin, *Tamarindus indica* seed polysaccharide, xanthan gum, carrageenan, high methoxyl pectin, low methoxyl pectin, guar gum, gum arabic, crystalline cellulose, arabinogalactan, karaya gum, tragacanth gum, alginic acid, albumin, casein, curdlan, β-glucan, gellan gum, and dextran.

As the oil agent, there are given volatile and non-volatile oil agents, solvents, and resins generally used in a cosmetic preparation. The oil agent may be a liquid, a paste, or a solid at normal temperature. The oil agent is preferably a liquid excellent in handling. Examples of the oil agent include: higher alcohols, such as cetyl alcohol, stearyl alcohol, isostearyl alcohol, lauryl alcohol, behenyl alcohol, octyldodecanol, and lanolin alcohol; fatty acids, such as isostearic acid, undecylenic acid, and oleic acid; esters, such as myristyl myristate, hexyl laurate, decyl oleate, isopropyl myristate, hexyldecyl dimethyloctanoate, glycerin monostearate, diethyl phthalate, ethylene glycol monostearate, and octyl oxystearate; hydrocarbons, such as liquid paraffin, Vaseline, and squalane; waxes, such as beeswax, lanolin, reduced lanolin, and carnauba wax; and oils and fats, such as mink oil, cacao butter, coconut oil, palm kernel oil, camellia oil, perilla oil, castor oil, olive oil, corn oil, jojoba oil, and rapeseed oil.

Examples of the powder include: dyes, such as Red No. 201, Yellow No. 4, Blue No. 1, and Black No. 401; lake dyes, such as Yellow No. 4 Al lake and Yellow No. 203 Ba lake; polymers, such as nylon powder, silk powder, silicone powder, cellulose powder, silicone elastomer spherical powder, and polyethylene powder; colored pigments, such as yellow iron oxide, red iron oxide, chromium oxide, carbon black, ultramarine blue, and Prussian blue; white pigments, such as zinc oxide and titanium oxide; extender pigments, such as talc, mica, sericite, and kaolin; pearl pigments, such as mica and titanium; metal salts, such as barium sulfate, calcium carbonate, magnesium carbonate, and magnesium silicate; inorganic powders, such as silica and alumina; bentonite; smectite; and boron nitride. There is no particular limitation on the shape (a spherical shape, a bar shape, a needle shape, a plate shape, an amorphous shape, a flake shape, or a spindle shape) of the above-mentioned powders.

Those powders may be surface-treated in advance through conventionally known surface treatment, such as fluorine compound treatment, silicone treatment, silicone resin treatment, pendant treatment, silane coupling agent treatment, titanium coupling agent treatment, oil agent treatment, N-acylated lysine treatment, polyacrylic acid treatment, metal soap treatment, amino acid treatment, inorganic compound treatment, plasma treatment, and mechanochemical treatment.

Examples of the other antibacterial agents include: imidazole-based antibacterial agents, such as thiabendazole and methyl 2-benzimidazolyl carbamate, and Preventol; carbanilide-based antibacterial agents, such as trichlorocarbanilide and cloflucarban; thiazole-based antibacterial agents, such as benzothiazole; triazine-based antibacterial agents, such as tebuconazole and kabinon; and biguanide-based antibacterial agents, such as chlorhexidine hydrochloride and polyhexamethylene biguanide. However, when those antibacterial agents are used in combination, it is desired to use those antibacterial agents carefully in consideration of, for example, irritation to a human body.

Examples of the moisturizer include: diethylene glycol monoethyl ether; biopolymers, such as deoxyribonucleic acid, mucopolysaccharides, sodium hyaluronate, sodium chondroitin sulfate, collagen, elastin, chitin, chitosan, and a hydrolyzed eggshell membrane; amino acids; sodium lactate; urea; sodium pyrrolidonecarboxylate; betaine; and whey.

Examples of the solvent include purified water, ethanol, light liquid isoparaffin, lower alcohols, ethers, LPG, fluorocarbons, N-methylpyrrolidone, fluoroalcohols, and alternatives to chlorofluorocarbons.

EXAMPLES

Now, the present invention is specifically described by way of Examples. In the following Examples and the like, "%" is by mass unless otherwise stated.

Examples 1 and 2 and Comparative Examples 1 to 11

<Preparation of Antibacterial and Antifungal Composition>

The antibacterial and antifungal composition formed of three components of the present invention and an antibacterial and antifungal composition formed of only two components, only one component, or other three components as Comparative Example were respectively prepared in accordance with mass ratios (total mass ratio of the components in each example is 1.0) of components shown in Table 1 and Table 2.

TABLE 1

| | Example | | Comparative Example | | | | |
|---|---|---|---|---|---|---|---|
| | 1 | 2 | 1 | 2 | 3 | 4 | 5 |
| A-1 | 0.33 | 0.33 | | 0.50 | | 0.50 | |
| B-1 | 0.33 | 0.33 | 0.50 | | 0.50 | | |
| C-1 | 0.33 | | | | | | 1.0 |
| C-2 | | 0.33 | | | | | |
| D-1 | | | 0.50 | 0.50 | | | |
| D-2 | | | | | 0.50 | 0.50 | |

TABLE 2

| | Comparative Example | | | | | |
|---|---|---|---|---|---|---|
| | 6 | 7 | 8 | 9 | 10 | 11 |
| A-1 | | | | 0.50 | 0.33 | 0.33 |
| B-1 | | | | | 0.33 | 0.33 |
| C-1 | | | | | | |
| C-2 | 1.0 | | | 0.50 | | |
| D-1 | | 1.0 | | | 0.33 | |
| D-2 | | | 1.0 | | | 0.33 |

<Used Compound>

Component (A)

A-1: 1,2-octanediol (caprylyl glycol)

Component (B)

B-1: 2-ethylhexyl glyceryl ether (ethylhexylglycerin)

Component (C)

C-1: phenethyl alcohol

C-2: benzyl alcohol

Component (D) (comparative component)

D-1: sodium benzoate

D-2: phenoxyethanol

<Minimum Growth Inhibitory Concentration (MIC) Test>

<Microorganisms to be Tested>

*E. coli: Escherichia coli* (bacterium) ATCC 8739

*P. aer: Pseudomonas aeruginosa* (bacterium) ATCC 9027

*S. aur: Staphylococcus aureus* (bacterium) ATCC 6538

*C. alb: Candida albicans* (yeast) ATCC 10231

*A. bra: Aspergillus brasiliensis* (mold) ATCC 16404

<Preparation of Microbial Liquid>

Bacteria were pre-cultured on a SCD liquid medium, and yeast and mold were pre-cultured on a glucose agar medium. After that, the concentration of viable cells in each liquid was adjusted to a $10^7$ cfu/mL level with a 0.9% NaCl aqueous solution, to thereby prepare test microbial liquids.

<Test Method>

0.020 μL of each of the test microbial liquids was dispensed onto a microplate, and further, 0.18 μL of each of antibacterial and antifungal solutions, in which the antibacterial and antifungal compositions prepared in Examples 1 and 2 and Comparative Examples 1 to 11 were adjusted to various concentrations with a culture medium, was added to the test microbial liquid, followed by stirring, to obtain a mixed solution. In this case, the pH of each of the antibacterial and antifungal solutions was from 6.89 to 7.24. Next, in each of the mixed solutions, culture was performed as follows. The bacterium mixed solution was cultured in a constant-temperature reservoir at 37° C. for 24 hours. The yeast mixed solution was cultured in the constant-temperature reservoir at 25° C. for 3 days. The mold mixed solution was cultured in the constant-temperature reservoir at 25° C. for 1 week. After that, through observation of the turbidity of each of the mixed solutions, the minimum concentration of the antibacterial and antifungal composition in the mixed solution in which opacity and presence of colonies and hyphae were not observed (the growth of the microorganisms to be tested was inhibited) was specified for each combination of the microorganisms and the antibacterial and antifungal solutions, and defined as a minimum growth inhibitory concentration (MIC) for the microorganisms. Further, the concentration at which the growth was inhibited for all five kinds of the microorganisms to be tested (that is, the highest concentration of the MICs of the five kinds of the microorganisms) was defined as a five-kind minimum growth inhibitory concentration (five-kind MIC). In addition, the appearance of the antibacterial and antifungal solution was evaluated as follows. The antibacterial and antifungal solution adjusted to the specified five-kind minimum growth inhibitory concentration was separately dropped onto a 4 mL tube and allowed to stand still. The appearance of the solution was visually observed and evaluated in accordance with the following criteria. The results are shown in Table 3 and Table 4.

Criteria for Evaluation of Solution Appearance o: transparent x: separation and turbidness are observed

TABLE 3

| | | Example | | Comparative Example | | | | |
|---|---|---|---|---|---|---|---|---|
| | | 1 | 2 | 1 | 2 | 3 | 4 | 5 |
| MIC | *E. coli* | 0.19 | 0.25 | 0.38 | 0.25 | 0.50 | 0.25 | 0.38 |
| | *P. aer* | 0.50 | 0.50 | >1.00 | 0.75 | 0.75 | 0.50 | 0.38 |
| | *S. aur* | 0.25 | 0.38 | 0.38 | 0.75 | 0.25 | 0.50 | 0.50 |
| | *C. alb* | 0.19 | 0.19 | 0.19 | 0.50 | 0.19 | 0.38 | 0.25 |
| | *A. bra* | <0.09 | 0.13 | 0.19 | 0.19 | 0.19 | 0.13 | <0.13 |
| | Five kinds | 0.50 | 0.50 | >1.00 | 0.75 | 0.75 | 0.50 | 0.50 |
| Evaluation of solution appearance | | ○ | ○ | X | X | X | X | X |

TABLE 4

| | | Comparative Example | | | | | |
|---|---|---|---|---|---|---|---|
| | | 6 | 7 | 8 | 9 | 10 | 11 |
| MIC | *E. coli* | 0.50 | >1.00 | 0.50 | 0.25 | 0.38 | 0.25 |
| | *P. aer* | 0.38 | >1.00 | 0.50 | 0.50 | 0.75 | 0.75 |
| | *S. aur* | 0.75 | >1.00 | 1.00 | 0.50 | 0.38 | 0.38 |
| | *C. alb* | 0.38 | >1.00 | 0.50 | 0.38 | 0.19 | 0.19 |
| | *A. bra* | 0.19 | >1.00 | 0.25 | 0.19 | 0.13 | 0.13 |
| | Five kinds | 0.75 | >1.00 | 1.00 | 0.50 | 0.75 | 0.75 |
| Evaluation of solution appearance | | ○ | ○ | ○ | X | X | X |

In the above-mentioned results, when the antibacterial and antifungal composition formed of three components of the present invention was used, satisfactory results were obtained both in the MIC evaluation and the appearance evaluation. On the other hand, when the antibacterial and antifungal composition formed of only two components, only one component, or other three components was used, for example, antibacterial and antifungal performance against various kinds of microorganisms to be evaluated based on the five-kind minimum growth inhibitory concentration was insufficient, and separation and turbidness were observed when the antibacterial and antifungal composition was formed into a solution. Thus, it was shown that there were problems in practical aspect. As described above, the antibacterial and antifungal composition of the present invention sufficiently exhibited antibacterial and antifungal performance against various kinds of microorganisms at a concentration lower than that of the conventional antibacterial and antifungal composition. In addition, when the antibacterial and antifungal composition of the present invention was formulated in a cosmetic preparation or a cleaning agent, cloudiness and precipitation were less liable to occur in the solution. Therefore, it was shown that the antibacterial and antifungal composition of the present invention had high practical utility as an antibacterial and antifungal composition.

Examples 3 to 6 and Comparative Example 12

<Formulation of Chemical Solution for Wet Wipes>

Chemical solutions for wet wipes of Examples 3 to 6 and Comparative Example 12 having compositions described below were prepared. Numerical symbols in Table 5 represent mass % with respect to the chemical solutions for wet wipes.

<Composition of Chemical Solution for Wet Wipes>

1,3-Butanediol 5 mass %

Disodium edetate 0.2 mass %

Allantoin 0.05 mass %

Sodium cocoamphoacetate 0.3 mass %

Antibacterial and antifungal composition 0.60 mass % to 0.90 mass % (blended as shown in Table 5)

Citric acid appropriate amount (adjusted to a pH of from 4.5 to 5.0)

Water balance

TABLE 5

| | Example 3 | Example 4 | Example 5 | Example 6 | Comparative Example 12 |
|---|---|---|---|---|---|
| A-1 | 0.20 | 0.25 | 0.30 | 0.30 | 0.30 |
| B-1 | 0.20 | 0.25 | 0.30 | 0.30 | 0.30 |
| C-1 | 0.20 | 0.25 | 0.30 | | |
| C-2 | | | | 0.30 | |

<Antibacterial and Antifungal Test>

20 g of each of the chemical solutions for wet wipes produced in Examples 3 to 6 and Comparative Example 12 and 0.20 mL of a microbial liquid in which the concentration of viable cells was at a $1.0\times10^8$ cfu/mL level were placed in a sterilized glass bottle with a lid having a capacity of 30 mL and homogeneously mixed. The day on which the glass bottle was stored in a constant-temperature reservoir at 25° C. was set to Day 0. Sampling was performed 2 days later and 7 days later. The concentration of the number of viable cells (unit: cfu/mL) was measured, and an antimicrobial activity value Log Reduction Value (LRV) was determined by the following expression. A larger value of the antimicrobial activity value LRV indicates that the antibacterial and antifungal performance is higher.

$$LRV=\log_{10}(\text{concentration of viable cells on Day 0/concentration of viable cells at time of sampling})$$

The antibacterial and antifungal performance was evaluated based on the determined antimicrobial activity value LRV in accordance with the following criteria. Each test result is shown in Table 6.

Criteria for Evaluation of Antibacterial and Antifungal Performance

◎: An antimicrobial activity value is 4.0 or more.

○: An antimicrobial activity value is 2.0 or more and less than 4.0.

Δ: An antimicrobial activity value is 1.0 or more and less than 2.0.

x: An antimicrobial activity value is less than 1.0.

The microorganisms used in the test are as described below.

A. bra: *Aspergillus brasiliensis* (mold) ATCC 16404

TABLE 6

| | | Example 3 | Example 4 | Example 5 | Example 6 | Comparative Example 12 |
|---|---|---|---|---|---|---|
| *A. bra* | 2 days later | Δ | ○ | ○ | Δ | X |
| | 7 days later | ◎ | ◎ | ◎ | ◎ | X |

It was understood from the above-mentioned results that any of the chemical solutions for wet wipes containing the antibacterial and antifungal composition formed of a combination of Component (A), Component (B), and Component (C) exhibited satisfactory antibacterial and antifungal performance. In addition, it was understood from the comparison between the results of Examples 3 to 6 and the results of Comparative Example 12 (using only Component (A) and Component (B)) that the antibacterial and antifungal effect was significantly enhanced through addition of Component (C). Thus, it was shown that the cosmetic preparation containing the antibacterial and antifungal composition containing Component (A), Component (B), and Component (C) exhibited high antibacterial and antifungal performance, in particular, antibacterial and antifungal performance against many kinds of bacteria, yeast, and fungi.

Examples 7 to 13 and Comparative Examples 13 and 14

<Evaluation of Enhancing Effect of Antibacterial and Antifungal Properties>

The antibacterial and antifungal composition formed of three components of the present invention and an antibacterial and antifungal composition formed of only two components as Comparative Example were respectively prepared in accordance with mass ratios (total mass ratio of the components in each example is 1.0) of components shown in Table 7. Each of the antibacterial and antifungal compositions was measured for a minimum growth inhibitory concentration for microorganisms by the same method as the test method of Example 1, and a fractional inhibitory concentration (FIC) index was calculated in accordance with the following equation. The FIC index is an index for evaluating the synergistic effect of antimicrobial properties in a composition formed of two or more components. A FIC index of less than 1 indicates that there is a synergistic effect, and a FIC index of more than 1 indicates that there is an antagonizing effect. The calculation results of the FIC index are shown in Table 7.

$$FIC=A_1/A_0+B_1/B_0+C_1/C_0$$

In the expression: $A_0$ represents a MIC value of Component (A) alone; $A_1$ represents a concentration of Component (A) in MIC when used together with another component; $B_0$ represents a MIC value of Component (B) alone; $B_1$ represents a concentration of Component (B) in MIC when used together with another component; $C_0$ represents a MIC value of Component (C) alone; and $C_1$ represents a concentration of Component (C) in MIC when used together with another component. In this case, as the MIC value of each component alone, a value measured by the same method as the test method of Example 1 was used, and as the concentration of each component when used together with another component, a value calculated based on the measured MIC value of the antibacterial and antifungal composition and a mass ratio of the corresponding component was used. The microorganisms used in the test are as described below.

C. alb: *Candida albicans* (yeast) ATCC 10231

TABLE 7

| | Example | | | | | | | Comparative Example | |
|---|---|---|---|---|---|---|---|---|---|
| | 7 | 8 | 9 | 10 | 11 | 12 | 13 | 13 | 14 |
| A-1 | 0.33 | 0.50 | 0.40 | 0.33 | 0.50 | 0.25 | 0.40 | 0.50 | 0.50 |
| B-1 | 0.33 | 0.25 | 0.40 | 0.33 | 0.25 | 0.50 | 0.40 | 0.50 | |
| C-1 | 0.33 | 0.25 | 0.20 | | | | | | |
| C-2 | | | | 0.33 | 0.25 | 0.25 | 0.20 | | 0.50 |
| FIC index | 0.84 | 0.82 | 0.86 | 0.75 | 0.75 | 0.82 | 0.80 | 0.88 | 1.26 |

As described above, it was found that, through combined use of Component (A), Component (B), and Component (C), the synergistic effect of antimicrobial properties was exhibited, and the synergistic effect higher than that in the case of using only Component (A) and Component (B) was exhibited (smaller FIC index was exhibited). Thus, it was indicated that the antibacterial and antifungal composition containing Component (A), Component (B), and Component (C), and the cosmetic preparation or the cleaning agent containing the antibacterial and antifungal composition exhibited high antibacterial and antifungal performance.

The invention claimed is:

1. An antibacterial and antifungal composition, comprising:

(A) 1,2-octanediolat;

(B) 2-ethylhexyl glyceryl ether; and (C) at least one aromatic alcohol selected from the group consisting of benzyl alcohol and phenethyl alcohol wherein a content of Component (A) is from 20 parts by mass to 50 parts by mass, a content of Component (B) is from 20 parts by mass to 50 parts by mass, and a content of Component (C) is from 15 parts by mass to 40 parts by mass, when a total mass of Component (A), Component (B), and Component (C) is 100 parts by mass.

2. A cosmetic preparation, comprising the antibacterial and antifungal composition of claim 1.

3. A cleaning agent, comprising the antibacterial and antifungal composition of claim 1.

4. A method of enhancing antibacterial and antifungal effects of Component (A) and Component (B) in a cosmetic preparation or a cleaning agent through use of Component (C), wherein the method comprises adding Component (A) which is a 1,2-octanediol, Component (B) which is a 2-ethylhexyl glyceryl ether, and Component (C) which is at least one aromatic alcohol selected from the group consisting of benzyl alcohol and phenethyl alcohol, to the cosmetic preparation or the cleaning agent, wherein a content of Component (A) is from 20 parts by mass to 50 parts by mass, a content of Component (B) is from 20 parts by mass to 50 parts by mass, and a content of Component (C) is from 15 parts by mass to 40 parts by mass, when a total mass of Component (A), Component (B), and Component (C) is 100 parts by mass.

* * * * *